(12) United States Patent
Thong

(10) Patent No.: US 6,339,724 B1
(45) Date of Patent: Jan. 15, 2002

(54) METHOD OF CONTROLLING THE STIMULATION AMPLITUDE OF A CARDIOLOGIC IMPLANT

(75) Inventor: Tran Thong, Portland, OR (US)

(73) Assignee: Biotronik Mess- und Therapiegeräte GmbH & Co. Ingenieurbüro Berlin, Berlin (DE)

( * ) Notice: Subject to any disclaimer, the term of this patent is extended or adjusted under 35 U.S.C. 154(b) by 0 days.

(21) Appl. No.: 09/604,294

(22) Filed: Jun. 26, 2000

(30) Foreign Application Priority Data

Jun. 24, 1999 (DE) .......................................... 199 29 091

(51) Int. Cl.[7] .............................................. A61N 1/368
(52) U.S. Cl. ............................................................ 607/28
(58) Field of Search .................................. 607/28, 8, 27

(56) References Cited

U.S. PATENT DOCUMENTS

| 5,766,230 A | | 6/1998 | Routh et al. | |
| 5,902,325 A | * | 5/1999 | Condie et al. | ................. 607/28 |

FOREIGN PATENT DOCUMENTS

| EP | 0 392 048 | 10/1990 |
| EP | 0 850 662 | 6/1998 |
| WO | 95 13845 | 5/1995 |
| WO | 99 20343 | 4/1999 |
| WO | 99 30777 | 6/1999 |

* cited by examiner

Primary Examiner—Kennedy Schaetzle
(74) Attorney, Agent, or Firm—Browdy and Neimark

(57) ABSTRACT

The invention is directed to a method of controlling the stimulation amplitude of a cardiologic implant which includes a stimulation impedance during delivery of left chamber stimulation pulses in the form of a measured value representative of the delivered stimulation pulse as a criterion for capture; determining and storing a comparative simulation impedance value representative of the stimulation; detecting an amplitude threshold for capture by determination of a significant change in the detected stimulation impedance as compared to the stored comparative stimulation impedance value; and then adjusting the stimulation amplitude on the basis of the detected amplitude threshold.

20 Claims, 1 Drawing Sheet

METHOD OF CONTROLLING THE STIMULATION AMPLITUDE OF A CARDIOLOGIC IMPLANT

BACKGROUND OF THE INVENTION

1. Field of the Invention

The invention relates to a method of controlling the stimulation amplitude of a cardiologic implant, which performs right and left chamber stimulation of the heart, using a left chamber stimulation electrode in a coronary vein and a counter electrode in the associated right cardiac chamber.

2. Background Art

As for the background of the of the invention, it can be said that cardiologic implants such a caradiac pacemakers or defibrillators pose the problem of requiring a supply of energy for as long as possible. The lifetime of an implant can be prolonged by an increase of battery capacity on the one hand and by the reduction of energy consumption on the other. This is the object of the invention.

Energy consumption of a cardiologic implant is determined by the amplitudes, to be controlled variably, of the stimulus pulses. The lower the amplitude is set, the lower is the energy consumption of the implant.

Problems are posed by the fact that of course, the amplitude cannot be set to any desired low level, since in this case the stimulus threshold of the organ that is supported by the implant is undershot, as a result of which there is no longer any successful stimulation. This is aggravated by the fact that on the one hand the stimulus thresholds from which on stimulation of the heart can take place successfully may differ strongly from patient to patient. On the other hand, the stimulus threshold from which on a stimulation pulse is successfully converted into a cardiac contraction also varies due to physiologic changes in one and the same patient in the course of time. Time constants of few hours up to months are usual for these changes.

For these reasons, today's cardiac pacemakers possess an automatic control system for the stimulation amplitude which, by appropriate detection processes and evaluation algorithms, keeps the stimulation amplitude as low as possible from energetic aspects and at a certain minimum level from the viewpoint of reliable medical care. U.S. Pat. No. 5,766,230 teaches to monitor the impedance course in time resolution during every delivery of a stimulation pulse by very complicated process and circuitry implementation. Capture, i.e. successful pulse stimulation which leads to cardiac contraction, is manifested, in the corresponding impedance measuring diagram, by a sudden drop or peak value, depending on the physiologic details and the circumstances in terms of measuring implementation. Since pulse recognition takes place in real time, it is possible, in the course of a pulse, to find out whether capture has been achieved. When capture is not recognized, a so-called "safety pulse" can be administered immediately, causing the desired cardiac contraction.

The above way of detection is accompanied with complicated apparatus implementation which is a drawback in particular with regard to the aim of keeping the energy consumption of the circuit as low as possible. On the one hand, the complicated implementation of real-time monitoring of the stimulation impedance requires some expenditure of energy, on the other hand this cited patent explicitly outlines that the stimulation amplitude is added by a high safety margin beyond the factually determined stimulation threshold. A numerical example quoted in U.S. Pat. No. 5,766,230 shows that with a stimulation threshold which occasions and is measured in the range of approximately 1.5 V, the factual stimulation voltage is in the range of approximately 2.8 V—which is almost twice the value. Consequently, a considerable potential of energy saving and thus prolongation of the lifetime is neglected in the prior art.

SUMMARY OF THE INVENTION

It is an object of the invention to specify a method of controlling the stimulation amplitude of a cardiologic implant, by means of which reliable stimulation, conform to therapy, of the implant supported organ is achieved, requiring reduced energy expenditure.

This object is attained in a method comprising the following steps:

- detection of the stimulation impedance during delivery of left chamber stimulation pulses in the form of a measured value representative of the respective stimulation pulse as a criterion for capture of a stimulation pulse;
- determination and storage of a comparative stimulation impedance value representative of the stimulation;
- detection of an amplitude threshold for capture of a stimulation pulse by determination of a significant change in the detected stimulation impedance as compared to the stored comparative stimulation impedance value; and
- adjustment of the stimulation amplitude on the basis of the detected amplitude threshold.

The invention proceeds from the fact that the implant supported heart is stimulated (also) on the left side. This makes use of the fact that higher amplitude thresholds are needed for stimulation of the left heart than for stimulation of the right heart, which fact is employed for instance in the cardiac pacemaker according to U.S. Pat. No. 5,766,230. Left cardiac chamber stimulation takes place for example by way of a ring electrode which is inserted into the coronary sinus and positioned in proximity to the left atrium or—if the electrode is inserted even further—near the left ventricle. Stimulation and perception may then take place as known per se either in a unipolar fashion between this electrode and the casing of the implant or in a bipolar fashion between this electrode and another electrode positioned for instance in the right atrium.

Upon left chamber stimulation of the heart, right chamber stimulation of the heart is initiated simultaneously, because right chamber stimulation takes place at lower stimulus thresholds. When the limit amplitude of left chamber stimulation is reached, right and left chamber stimulation of the heart takes place, left chamber capture not being ensured, because stimulation takes place closely below the amplitude threshold. This does, however, not pose any problems in light of the fact that stimulation only of the right cardiac chambers is unobjectionable from aspects of hemodynamics. Left chamber contraction will take place automatically, owing to the natural propagation after right chamber stimulation, although this will be a bit later than in the case of simultaneous stimulation. This natural stimulus propagation is the reason why stimulation by conventional pacemakers usually takes place exclusively in the right cardiac chambers.

Since the method according to the invention makes use of capture that occurs in the left cardiac chamber as a measure for the adjustment of the stimulation amplitude, a natural interval towards the absolute right chamber stimulus threshold is detected, below which no capture will take place. This is the interval which the prior art intends to ensure by the use of a safety margin. This prior art safety margin is selected more or less arbitrarily, based on experience, whereas the method according to the invention makes us of a genuine physiologic parameter, namely left chamber capture.

In this case, the comparative stimulation impedance value which is representative of stimulation can be detected, indicated and stored as a reference value upon initial operation of the cardiologic implant. Preferably, the comparative impedance value is detected continuously as an individual or average value of impedance over several stimulation pulses; it is then updated and stored.

In this case, detection according to the invention of the amplitude threshold may take place by continuous comparison with the comparative impedance value on the basis of a significant reduction in the stimulation impedance as opposed to the comparative impedance value when left heart chamber capture is not achieved. This implies that operation at a uniform stimulation amplitude will take place in the case of continuous capture.

By alternative, the amplitude threshold can virtually be scanned by successively increasing the stimulation pulse amplitude until left chamber capture is detected by recognition of a significant increase of the stimulation impedance as compared to the comparative impedance value.

If desired for special forms of therapy, the stimulation amplitude can be set to overshoot the detected amplitude threshold by a buffer difference. But due to the fact that left cardiac chamber capture is used as a basis for the adjustment of the amplitude threshold, this safety margin may be by far lower than the prior art safety margin where a factor 2 is employed.

In a preferred embodiment of the method according to the invention, when a loss of left chamber capture occurs, a reliable routine can be employed for the amplitude threshold to be suited to the obvious change of conditions. Accordingly, the stimulation amplitude is set to a maximum and then decreased successively during the subsequent stimulation cycles until again a loss of capture is recognized. This condition defines the freshly formed amplitude threshold which, due to its nature of constituting a limit value towards left chamber stimulation, does not necessarily ensure capture on this side of the heart; however, a sufficient, physiologically defined interval towards the right chamber stimulation threshold is maintained, leading to reliable operation of the implant.

For an increase in reliability, a preferred development of the method provides that, after recognition of a failure of capture, the stimulation amplitude can be set to a maximum for at least one pulse.

An especially preferred development of the method according to the invention provides for a tripolar stimulation arrangement comprising a left chamber stimulation electrode in a coronary vein, a right chamber stimulation electrode in an associated right cardiac chamber and a counter electrode. Accordingly, during detection of the amplitude threshold, the stimulation impedance can be monitored for any significant increase in impedance upon transition from right chamber stimulation to both right and left chamber stimulation and the stimulation amplitude can be set to the amplitude value determined upon transition. This layout of the method according to the invention makes optimal use of the possibilities of a tripolar electrode arrangement. Owing to the differentiation, ensured by the tripolar arrangement, between exclusively right chamber stimulation and both right and left chamber stimulation, it is unobjectionable not to raise the amplitude value of the amplitude threshold upon detection of a failure of left chamber capture. This is a special step towards attaining the object, mentioned at the outset, of as low as possible an expenditure of energy.

By contrast to the prior art discussed, the invention enables the measured stimulation impedance value representative of the respective stimulation pulse to be detected by continuously recording and evaluating current and voltage as an average value integrated or averaged via the pulse. Implementing the method according to the invention does not require any complicated real-time monitoring of the pulse, only an average value has to be processed.

In keeping with a further simplification, this value can also be determined by the stimulation current being measured only at a defined instant after the start of the pulse and, for computation of the impedance, being brought in relation to the stimulation voltage set on the side of the pacemaker.

Further features, details and advantages of the invention will become apparent from the ensuing example of an exemplary embodiment, taken in conjunction with the attached drawing.

DESCRIPTION OF THE PREFERRED EMBODIMENT

Figure 1:
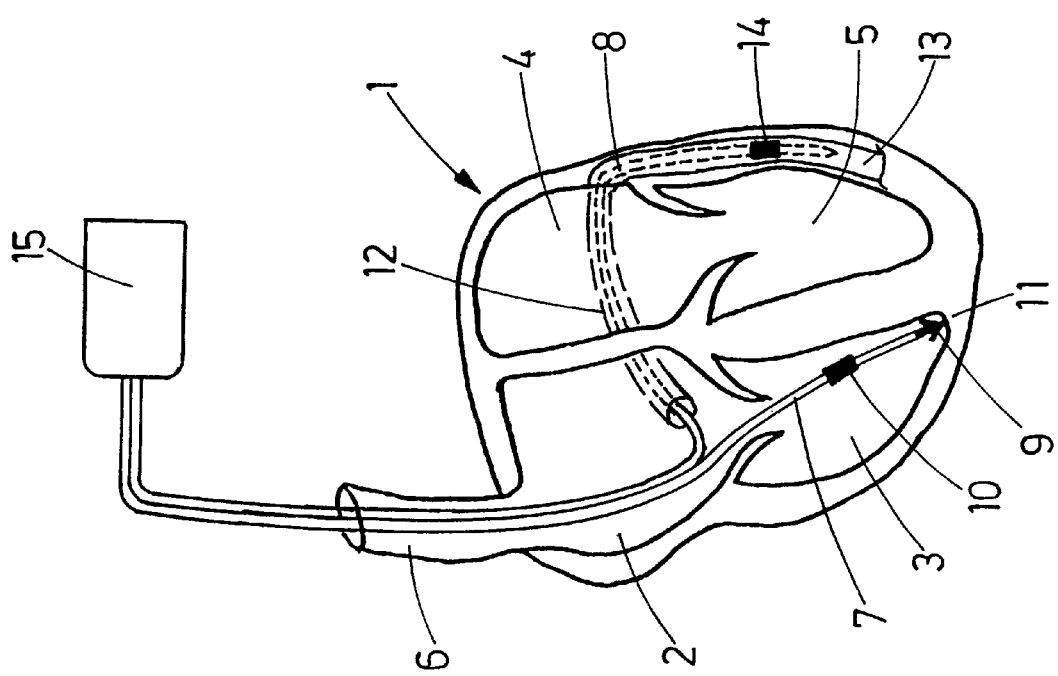
FIG. 1 is a diagrammatic illustration of a pacemaker supported heart comprising a tripolar electrode arrangement.

The drawing shows a diagrammatic section of a heart designated by 1 and comprising a right atrium 2, right ventricle 3, left atrium 4, and left ventricle 5. Two catheters 7, 8 are led via the vena cava 6 into the heart, the catheter 7 of which is advanced via the right atrium 2 into the right ventricle 3. Mounted on this catheter 7 are a tip electrode 9 and a ring electrode 10. The tip electrode 9 is anchored at the pointed end of the right ventricle 3 in the myocardium 11. The ring electrode 10 floats freely in the blood stream within the right ventricle 3.

The second catheter 8 is advanced via the coronary sinus 12 as far as to the ensuing great cardiac vein 13, whereby another ring electrode 14 is positioned in this great cardiac vein 13.

The two catheters 7, 8 lead to a cardiac pacemaker 15 which is conventionally implanted subcutaneously and to which the electrodes 9, 10, 14 are connected via corresponding inlets. The cardiac pacemaker 15 is of customary design, a microprocessor-based central control unit with a corresponding control program implemented therein being part of it in addition to, for instance, a suitable energy supply system on the basis of a battery and a telemetry data transmission unit for pacemaker programming and data fetching from outside. This control program converts certain routines and methods for the delivery of stimulation pulses of certain pulse shapes, stimulation amplitudes, time sequences etc. as necessary for the therapy of malfunctions of the heart 1.

In this regard, also a method, according to the invention, for the control of the stimulation amplitude of the cardiac pacemaker 15 is implemented in the control program of the pacemaker. This proceeds from a tripolar arrangement with the tip electrode 9 and the ring electrode 14 as cathodes and the ring electrode 10 as an anodic counter electrode. The result is left and right chamber ventricular—i.e. "biventricular"—stimulation of the heart by the delivery of corresponding stimulation pulses. These stimulation pulses are to be adjusted to a certain stimulation amplitude, to which end a certain amplitude threshold must be determined, which ensures reliable cardiac stimulation. To this end, the stimulation impedance is detected during the delivery of stimulation pulses via the electrodes 9, 14, 10 by the stimulation current administered via the tip electrode 9 and the ring electrode 14 being measured at a defined instant, for instance 30 $\mu$sec after the start of the stimulation pulse of a duration of up to 2 msec, and being brought in relation to the stimulation voltage adjusted on the side of the pacemaker for impedance computation. Medical series of measurements have shown that the stimulation impedance was, for example, 230 Ohm, in the case of right chamber capture, whereas it was 290 Ohm, in the case of left and right chamber capture. A corresponding comparative impedance value can be stored in a corresponding storage in the microprocessor control system of the pacemaker.

During operation of the pacemaker, the detected stimulation impedance is compared with the stored comparative value and, in the case of a significant change during a stimulation pulse, the stimulation amplitude used is detected as an amplitude threshold for the successful delivery of a stimulation pulse. The stimulation amplitude is then adjusted correspondingly.

During operation, the comparative impedance value can be determined as an average over several stimulation pulses; it is updated correspondingly and stored. This is a quasi passive detection of the amplitude threshold, because measuring takes place during operation.

Active detection can be carried out on the basis of the above-mentioned increase of stimulation impedance in the case of right chamber capture or right and left chamber capture, respectively, by an amplitude threshold being determined by successive increase of the amplitude of the stimulation pulses until capture is detected by a significant increase of stimulation impedance being determined. In doing so, the transition from a lower impedance value in the case of only right chamber capture to the higher impedance value in the case of right and left chamber capture is monitored.

The stimulation amplitude is set to the amplitude value determined upon the transition so that the cardiac pacemaker virtually always works on the borderline toward right and left chamber capture. Fluctuations of the necessary stimulus thresholds may cause the stimulation amplitude to be too low for right and left chamber stimulation, but since it overshoots the level necessary for right chamber stimulation by a sufficient measure, this right chamber stimulation is ensured virtually at any moment. In this regard, there is no need of an increase of the amplitude value in the case of a failed left chamber capture.

If only right chamber stimulation or no stimulation at all is found, the stimulation amplitude for the subsequent pulse may also be set to a maximum and then be reduced successively during further ensuing pulses. A status is occasioned, in which stimulation takes place at a high lever of energy, i.e. both right and left chamber stimulation. The borderline between right and left chamber stimulation and exclusively right chamber stimulation is determined by the mentioned monitoring of the impedance value, where-after the amplitude threshold is set to this limit value. This is an adjustment to the new amplitude threshold.

What is claimed is:

1. A method of controlling a stimulation amplitude of a cardio-logic implant, which performs right and left chamber stimulation of a heart, using a left chamber stimulation electrode (14) in a coronary vein (13), comprising the following steps:

detecting a stimulation impedance during delivery of left chamber stimulation pulses in the form of a measured value representative of the delivered stimulation pulse as a criterion for capture;

determining and storing a comparative stimulation impedance value representative of a stimulation;

detecting an amplitude threshold for capture by determining a significant change in the detected stimulation impedance as compared to the stored comparative stimulation impedance value; and adjusting the stimulation amplitude on the basis of the detected amplitude threshold.

2. A method according to claim 1, further comprising the steps of detecting the comparative impedance value continuously as an individual or average value over several stimulation pulses and then updating and storing said comparative impedance value.

3. A method according to claim 1, further comprising the step of detecting the amplitude threshold on the basis of a significant reduction of the stimulation impedance as compared to the comparative impedance value due to a loss of capture.

4. A method according to claim 1, further comprising the step of actively detecting the amplitude threshold by successively raising the amplitude of the stimulation pulses until capture is recognized by detecting a significant increase of the stimulation impedance as compared to the comparative impedance value.

5. A method according to claim 4, comprising the step of regularly repeating amplitude threshold detection for the amplitude threshold to be updated continuously.

6. A method according to claim 1, wherein the stimulation amplitude is set to overshoot the amplitude threshold by a buffer difference.

7. A method according to claim 1, wherein after non-capture has been detected, the stimulation amplitude for an ensuing pulse is set to a maximum and then reduced successively until a failure of capture defines the amplitude threshold.

8. A method according to claim 1, wherein after recognizing non-capture, the stimulation amplitude is set to a maximum for at least one pulse.

9. A method of controlling a stimulation amplitude of a cardiologic implant which performs right and left chamber stimulation of a heart, using a tripolar stimulation arrangement comprising a left chamber stimulation electrode (14) in a coronary vein (13), a right chamber simulation electrode (9) in an associated right cardiac chamber (3) and a counter electrode (10), comprising the following steps:

detecting a stimulation impedance during delivery of left chamber stimulation pulses in form of a measured value representative of the delivered stimulation pulse as a criterion for capture;

determining and storing a comparative stimulation impedance value representative of stimulation;

detecting an amplitude threshold for capture by determining a significant chance in the detected stimulation impedance as compared to the stored comparative stimulation impedance value; and adjusting the stimulation amplitude on the basis of detected amplitude threshold, wherein during the detection of the amplitude threshold, the stimulation impedance is monitored for an occurrence of a significant impedance increase upon transition from right chamber rapture to both left and right chamber capture and wherein the stimulation amplitude is adjusted to an amplitude value found upon the transition.

10. A method according to claim 9, wherein the amplitude value is not raised upon detection of a failure of left chamber capture.

11. A method of controlling a stimulation amplitude of a cardiologic implant, which performs right and left chamber stimulation of a heart, using a left chamber stimulation of a heart, using a left chamber stimulation electrode (14) i a coronary vein (13) and a counter electrode (10), in a right chamber (3) comprising the following steps:

detecting a stimulation impedance during delivery of left chamber stimulation pulses in form of a measured value representative of the delivered stimulation pulse as a criterion for capture;

determining and storing a comparative stimulation impedance value representative of stimulation;

detecting an amplitude threshold for capture by determining a significant change in the detected stimulation impedance as compared to the stored comparative stimulation impedance value; and adjusting the stimulation amplitude on the basis the detected amplitude threshold, wherein as a measured impedance value which is representative of the delivered stimulation pulse, an impedance average is detected, which is integrated or averaged by current and voltage being continuously recorded and evaluated over the pulse.

12. A method according to claim 1, wherein for determination of the measured impedance value which is representative of the delivered stimulation pulse, a stimulation current is measured at a defined instant after a start of the pulse and the impedance is calculated from said measured stimulation current and a stimulation voltage adjusted at the implant by Ohm's Law.

13. A method according to claim 9, comprising the step of active detection of the amplitude threshold by successively raising the amplitude of the stimulation pulses until capture is recognized by detection of a significant increase of the stimulation impedance as compared to the comparative impedance value.

14. A method according to claim 9, wherein the stimulation amplitude is set to overshoot the amplitude threshold by d buffer difference.

15. A method according to claim 9, wherein alter non-capture has been detected, the stimulation amplitude for an ensuing pulse is set to a maximum and then reduced successively until a failure of capture defines the amplitude threshold.

16. A method according to claim 9, wherein after recognition of non-capture, the stimulation amplitude is set to a maximum for at least one pulse.

17. A method according to claim 11, comprising the step of active detection of the amplitude threshold by successively raising the amplitude of the stimulation pulses until capture is recognized by detection of a significant increase of the stimulation impedance as compared to the comparative impedance value.

18. A method according to claim 11, wherein the stimulation amplitude is set to overshoot the amplitude threshold by a buffer difference.

19. A method according to claim 11, wherein after non-capture has been detected, the stimulation amplitude for an ensuing pulse is set to a maximum and then reduced successively until a failure of capture defines the amplitude threshold.

20. A method according to claim 11 wherein after recognition of non-capture, the stimulation amplitude is set to a maximum for at least one pulse.

* * * * *